United States Patent [19]
Kohn et al.

[11] Patent Number: 4,520,199
[45] Date of Patent: * May 28, 1985

[54] ALKOXY SUBSTITUTED PHENOXY ALKANOIC ACID ESTERS

[75] Inventors: Gustave K. Kohn, Palo Alto; Joe T. Bamberg, Redwood City, both of Calif.

[73] Assignee: Zoecon Corporation, Palo Alto, Calif.

[ * ] Notice: The portion of the term of this patent subsequent to Nov. 20, 2001 has been disclaimed.

[21] Appl. No.: 407,685

[22] Filed: Aug. 13, 1982

[51] Int. Cl.³ .................... C07D 213/64; A01N 43/40
[52] U.S. Cl. .................................... 546/302; 546/157; 546/297; 546/312; 544/354; 548/166; 548/221; 560/61; 560/62; 560/21

[58] Field of Search ..................... 546/312, 297, 302

[56] References Cited

U.S. PATENT DOCUMENTS

| 3,379,752 | 4/1968 | Bolhofer | 260/473 |
| 4,134,751 | 1/1979 | Nishiyama | 71/94 |
| 4,216,007 | 8/1980 | Nishiyama | 71/94 |
| 4,348,221 | 9/1982 | Szczepanski | 71/94 |

Primary Examiner—Alan L. Rotman
Attorney, Agent, or Firm—Hana Dolezalova; Jacqueline S. Larson

[57] ABSTRACT

3-Alkoxy-4-substituted phenoxy alkanoic acid esters, derivatives thereof, and the use thereof for the control of weeds.

6 Claims, No Drawings

ALKOXY SUBSTITUTED PHENOXY ALKANOIC ACID ESTERS

This invention relates to novel 3-alkoxy-4-substituted phenoxy alkanoic acid esters, derivatives thereof, and the use thereof for the control of weeds.

The novel compounds of the present invention are represented by the following formula (A):

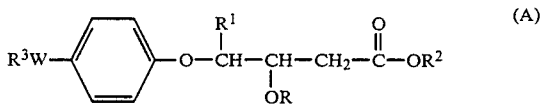

wherein,
R is lower alkyl;
$R^1$ is hydrogen or lower alkyl;
$R^2$ is lower alkyl, lower alkenyl or lower alkynyl;
W is oxygen, sulfur or amino; and
$R^3$ is one of the groups

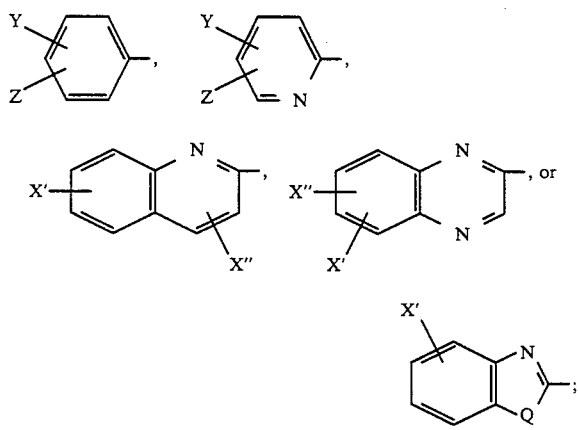

in which,
each of Y and Z is independently selected from hydrogen, lower alkyl, lower haloalkyl, lower alkoxy, lower haloalkoxy, bromo, chloro, fluoro, nitro and cyano;
each of X' and X" is independently selected from hydrogen, fluoro, chloro, bromo, trifluoromethyl, methoxy or nitro, provided that both X' and X" cannot be trifluoromethyl, methoxy or nitro; and
Q is oxygen or sulfur.

In the description and claims hereinafter, each of R—$R^3$, Q, W, X', X", Y and Z is as defined above, unless otherwise specified.

The compounds of formula (A) can be synthesized by the reaction of an alcohol of formula (I) with a diazoalkyl in an organic solvent inert to the reaction, such as ether, and catalyzed by silica gel, following the procedure described by K. Ohno et al., *Tetrahedron Letters* No. 45, p. 4405 (1979).

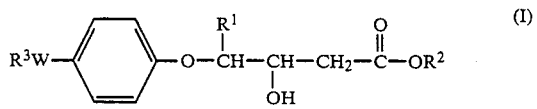

The alcohols of formula (I) and their preparation are described by S. Lee, U.S. Pat. No. 4,408,076, the entire disclosure of which is incorporated herein by reference.

The following terms, whereever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compound, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice wheat, barlet, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

Diazomethane (2.8 g) in ether (100 ml) is added to ethyl 4-[4-(4-trifluoromethylphenoxy)phenoxy]-3-hydroxypentanoate (1.88 g, 3.75 mmol) in ether (5 ml) under $N_2$ and in an ice bath. Small amounts of chromatographic silica gel are added to the mixture in the ice bath until the color disappears. The mixture is then stirred overnight with cooling. The silica gel is removed by filtration and the organic phase is dried and concentrated. The crude product is purified by preparative thin layer chromatography to yield ethyl 4-[4-(4-trifluoromethylphenoxy)phenoxy]-3-methoxypentanoate (cpd. 1 in Table A). MS m/e 412 (m+).

EXAMPLE 2

Following the procedure of Example 1, each of the alcohols under column I is reacted with diazomethane to give the corresponding compound in Table A.

I 2. ethyl 4-[4-(2-chloro-4-trifluoromethylphenoxy)phenoxy]-3-hydroxypentanoate
3. ethyl 4-[4-(2-nitro-4-trifluoromethylphenoxy)phenoxy]-3-hydroxypentanoate
4. ethyl 4-[4-(2,4-dichlorophenoxy)phenoxy]-3-hydroxypentanoate
5. ethyl 4-[4-(4-trifluoromethylphenoxy)phenoxy]-3-hydroxybutanoate
6. methyl 4-[4-(4-trifluoromethylphenoxy)phenoxy]-3-hydroxypentanoate

EXAMPLE 3

Following the procedure of Example 1, ethyl 4-[4-(4-trifluoromethylphenoxy)phenoxy]-3-hydroxypentanoate is reacted with each of diazoethane and diazopropane to give the corresponding 3-alkoxy compound (cpd. 7 and cpd. 8, respectively, in Table A).

TABLE A (II)

$$\text{Z}\underset{\text{Y}}{\diagdown}\text{—phenyl—O—phenyl—O—CH(R}^1\text{)—CH(OR)—CH}_2\text{—C(=O)—OR}^2$$

| Cpd. | Z   | Y   | $R^1$ | R         | $R^2$    |
|------|-----|-----|-------|-----------|----------|
| 1    | CF3 | H   | CH3   | CH3       | CH2CH3   |
| 2    | CF3 | Cl  | CH3   | CH3       | CH2CH3   |
| 3    | CF3 | NO2 | CH3   | CH3       | CH2CH3   |
| 4    | Cl  | Cl  | CH3   | CH3       | CH2CH3   |
| 5    | CF3 | H   | H     | CH3       | CH2CH3   |
| 6    | CF3 | H   | CH3   | CH3       | CH3      |
| 7    | CF3 | H   | CH3   | CH2CH3    | CH2CH3   |
| 8    | CF3 | H   | CH3   | CH2CH2CH3 | CH2CH3   |

EXAMPLE 4

Following the procedure of Example 1, each of the 3-hydroxy compounds under column 2 is reacted with diazomethane to give the corresponding 3-methoxy pentanoate.

II 9. ethyl 4-[4-(3-chloro-5-trifluoromethyl-2-pyridyloxy)phenoxy]-3-hydroxypentanoate
10. ethyl 4-[4-(5-trifluoromethyl-2-pyridyloxy)phenoxy]-3-hydroxypentanoate
11. ethyl 4-[4-(6-fluoro-2-quinolyloxy)phenoxy]-3-hydroxypentanoate
12. ethyl 4-[4-(6-chloro-2-quinoxalinyloxy)phenoxy]-3-hydroxypentanoate
13. ethyl 4-[4-(benzo-1,3-oxazolyl-2-oxy)phenoxy]-3-hydroxypentanoate

What is claimed is:

1. A compound of the following formula (A):

$$R^3W\text{—phenyl—O—CH(R}^1\text{)—CH(OR)—CH}_2\text{—C(=O)—OR}^2 \quad (A)$$

wherein,
R is lower alkyl;
$R^1$ is methyl;
$R^2$ is lower alkyl, lower alkenyl or lower alkynyl;
W is oxygen; and
$R^3$ is $$\text{Y, Z-substituted pyridinyl};$$

in which,
each of Y and Z is independently selected from hydrogen, trifluoromethyl, bromo, chloro, fluoro and nitro.

2. A compound of the following formula according to claim 1:

$$R^3\text{—O—phenyl—O—CH(CH}_3\text{)—CH(OR)—CH}_2\text{—C(=O)—OR}^2$$

wherein $R^2$ is lower alkyl.

3. A compound according to claim 2 wherein $R^3$ is $$\text{Y, Z-substituted pyridinyl};$$

in which Y is hydrogen or chloro and Z is chloro or trifluoromethyl.

4. A compound according to claim 3 wherein Y is chloro and R is methyl.
5. A compound according to claim 3 wherein Y is chloro, Z is trifluoromethyl and R is methyl.
6. A compound according to claim 3 wherein Y is hydrogen, Z is trifluoromethyl and R is methyl.

* * * * *